United States Patent [19]
White et al.

[11] Patent Number: 5,604,113
[45] Date of Patent: Feb. 18, 1997

[54] CELLS HAVING ONCOGENE-SUPPRESSED P53-MEDIATED APOPTOSIS AND METHODS OF USE TO IDENTIFY ANTI-ONCOGENIC COMPOUNDS

[75] Inventors: Eileen White, Belle Mead, N.J.; Shuin-Kwei Chiou, N. Potomac, Md.; Huey-Jen L. Lin, Princeton, N.J.

[73] Assignee: Rutgers University, Piscataway, N.J.

[21] Appl. No.: 224,209

[22] Filed: Apr. 7, 1994

[51] Int. Cl.$^6$ ................. C12Q 1/02; C12N 5/06
[52] U.S. Cl. ................ 435/29; 435/325; 435/353
[58] Field of Search .................. 435/7.23, 6, 29, 435/240.2

[56] References Cited

FOREIGN PATENT DOCUMENTS 9213091  8/1992  WIPO .

OTHER PUBLICATIONS

C. Dive and J. A. Hickman, Br. J. Cancer (1991): 64: 192–196.
Debbas, M. and E. White, Genes Dev. (1993): 7: 546–554.
L. Rao, M. Debbas, P. Sabbatini, D. Hockenberry, S. Korsmeyer, and E. White (1992): PNAS 89: 7742–7746.
Michalovitz, D. O. Halevy, and M. Oren Cell (1990) 62: 671–681.

*Primary Examiner*—Mindy Fleisher
*Assistant Examiner*—Terry A. McKelvey
*Attorney, Agent, or Firm*—Kenyon & Kenyon

[57] ABSTRACT

The present invention is a method for determining if a compound potentially modulates the ability of a putative oncogene to suppress p53-mediated effects, comprising (A) adding an amount of said compound to genetically engineered cells that express (i) a gene product that induces p53 mediated apoptosis; (ii) a gene product for a p53 gene, wherein either the gene or the gene product are externally controllable; and (iii) a putative oncogene that inhibits the effect of the gene product that induces p53 mediated apoptosis, and (B) examining said cells to determine whether apoptosis has occurred. In particular, the invention provides a method wherein said gene product that induces p53 mediated apoptosis is adenovirus gene E1A, wherein said externally controllable p53 gene product is a temperature-sensitive mutant of p53, and wherein the putative oncogene is selected from the group bcl-2, ras, or the adenovirus E1B(19K) gene. In addition, the invention provides genetically engineered cell lines that can be used to carry out the methods described.

10 Claims, 7 Drawing Sheets

CELLS HAVING ONCOGENE-SUPPRESSED P53-MEDIATED APOPTOSIS AND METHODS OF USE TO IDENTIFY ANTI-ONCOGENIC COMPOUNDS

The U.S. Government has a paid up license in this invention, and the right in limited circumstances to require the patent owner to license others on reasonable terms, as provided for by the terms of grant No. CA53370 from the National Institutes of Health.

FIELD OF THE INVENTION

The present invention relates generally to methods for the identification of chemical compounds that are able to modify the apoptosis-inhibiting effects of putative oncogenes, and hence may be of value in the treatment of cancer. The invention also relates to genetically engineered cell lines useful for performing the methods of the invention.

BACKGROUND OF THE INVENTION

Apoptosis, or programmed cell death, is the process by which a cell will actively self-destruct in response to certain developmental stimuli. The apoptotic death process is associated with profound but well defined morphological changes in the cell, including intranucleosomal DNA fragmentation. However, apoptosis is distinguishable from necrosis, which is cell death that occurs in response to physical injury.

Apoptosis is a fundamentally important process in the regulation of cell proliferation required for normal cell and organ development (24) and regulation of apoptosis in required to maintain the ongoing stability of biological systems. Apoptosis also modulates viral pathogenesis and latency (10,16, 35). In addition, apoptosis has been strongly suggested to serve as a natural defense against cancer (21). One reason for this belief is that the molecular events that result in apoptosis are intimately related to the molecular events that lead to the development of cancer ("transformation"). Another reason is that cancerous states are often manifested by unrestricted cell division, and by the failure of cells to undergo apoptosis.

Although a number of genes that either induce or suppress apoptosis have been identified, regulation of apoptosis and its connection to transformation is poorly understood. It is known that expression of genes that appear to deregulate cell growth, such as E1A (1, 25) and c-myc (7, 26), can initiate the apoptotic response. It is also known that negative growth signals such as growth factor withdrawal (24) or induction of p53 levels (17) are similarly associated with apoptosis. These findings suggest that apoptosis may arise because of incompatible or conflicting growth signals (4, 27). These conflicting signals may arise during the transformation process.

It is also known that two putative oncogenes, bcl-2 (12), the adenovirus E1B 19K gene (1, 4, 25), can inhibit apoptosis. In transformation assays, E1B will cooperate with E1A (33), and bcl-2 will cooperate with both E1A (25) and c-myc (2, 8, 31). By such cooperation, the cellular stimulation that generally results in apoptosis is induced, but apoptosis is inhibited; these effects appear to result in the hyperactive cellular metabolism and excessive cell division that are characteristic of the cancerous state.

The nuclear phosphoprotein known as p53 has a number of recognized functions. First, p53 has a specific DNA binding capability that can both positively and negatively regulate transcription (reviewed in 29). Second, p53 is recognized as a tumor suppressor gene. Evidence for p53's role in suppressing cancer include the finding that mutations in p53 are the most prevalent genetic alterations in found in human tumors (13, 32), and the finding that the loss of p53 function greatly accelerates the frequency of tumor formation in humans (19) and animal models (6). Third, there is evidence that p53 regulates control of the cell cycle (5, 20). Fourth, p53 may be involved in apoptosis in some (but not all) cells (28). These last two functions may be related. For example, in response to DNA damage, p53 levels are increased, and p53 acts as either a cell cycle check point, producing G1 arrest to permit repair (15), or as a trigger for apoptosis (3, 18).

Prior to the discoveries upon which the present invention is based, how the apoptosis-inducing effects of E1A were mediated, or how the apoptosis-inhibiting effects of putative oncogenes E1B(19K), bcl-2, and ras were mediated, were not known.

ADVANTAGES AND SUMMARY OF THE INVENTION

Identifying drugs that are potentially useful in the treatment of cancer historically has been hampered by the lack of suitable model systems to allow for meaningful yet rapid screening. Animal models do not exist for many forms of human cancer, and cancer cell cultures are not always available for a given type of cancer. In addition, even when models or tumor cultures are available, because actual cancer cells have such greatly altered cellular functions it is often not possible to discern at what cellular or chemical level different candidate compounds might be acting.

In addition, the recognition that certain genes are involved in the processes of viral infection and in transformation of cancer cells has created a heightened research interest in such genes. The model systems that are within the scope of the present invention offer outstanding opportunities to probe such genes for their cellular and metabolic activities. The use of these systems for examining the ability of putative oncogenes to suppress p53-mediated apoptosis is clearly a valuable use. In addition, this invention Could also be used as a research tool in learning about the dynamics of p53 induction of apoptosis. It could also be used to study p53-induced growth arrest; cells expressing E1A, p53, and bcl-2, for example, are arrested but not apoptotic. Such cells therefore offer a stable study system in which the apoptotic and arrest phenomena caused by p53 have been effectively separated. Furthermore, such model systems could also be used to study how E1A and other, similarly acting genes are able to induce apoptosis. Since the apoptosis can be reversibly arrested by expression of a putative oncogene, such cells can be studied to understand what the E1A signal is, and how p53 gene product responds to it.

In light of the foregoing, it is one object of this invention, to provide a simplified model system in which drugs that can alter the activity of putative oncogenes can be identified.

More specifically, it is an object of this invention to provide a screening method to identify chemical compounds that modify the ability of putative oncogenes to inhibit p53 mediated apoptosis.

It is also an object of this invention to provide a method of screening for anti-oncogenic drugs that may be useful in the treatment of carcinoma and other transformed states.

It is further an object to provide genetically engineered cell lines useful in the above-mentioned methods.

It is also an object of this invention to provide model systems that can be used as research tools for studying the molecular dynamics of genes that induce apoptosis, p53, and genes that suppress p53-mediated apoptosis. Furthermore, it is also an object of this invention to provide research tools useful in further understanding mechanisms involved in transformation and viral infectivity.

In one embodiment of the invention, a method is provided for determining if a compound potentially inhibits the ability of a putative oncogene to suppress p53-mediated apoptosis, comprising (A) adding an amount of said compound to genetically engineered cells that express (i) a gene product that induces p53 mediated apoptosis; (ii) a gene product of a p53 gene, wherein either the gene or the gene product are externally controllable; and (iii) a putative oncogene that inhibits the effect of the gene product that induces p53 mediated apoptosis, and (B) examining said cells to determine whether apoptosis has occurred or proliferation has been controlled or induced.

In another embodiment, the invention provides a method wherein said gene product that induces p53 mediated apoptosis is adenovirus gene E1A, and wherein said externally controllable p53 gene product is a temperature-sensitive mutant of p53, and where the putative oncogene is bcl-2, ras, or the adenovirus E1B(19K) gene.

Additional embodiments of the invention are methods comprising the foregoing methods carried out in combination with the use of suitable controls, such that it can be ascertained whether a candidate compound acts at the level of the putative oncogene or its expression product and not by non-specific cytotoxicity, or by inhibiting the gene that induces p53 mediated apoptosis or the p53 gene, their expression, or their expression products.

In yet another embodiment, the present invention provides a method for screening candidate compounds for an ability to act as anti-oncogenic drugs, wherein an effective amount of a compound is added to genetically engineered cells that express: a gene product that induces p53 mediated apoptosis; an externally regulatable p53 gene product; and a putative oncogene that inhibits the effect of the first-mentioned gene product. These cells are then examined to determine whether apoptosis has occurred, and the occurrence of apoptosis indicates that the compound potentially inhibits the ability of said putative oncogene to suppress said p53-mediated effects. Control samples are then similarly treated, to determine if the compound acts at the level of the oncogene or its expression product and not by non-specific cytotoxicity, or by inhibiting the gene that induces p53 mediated apoptosis or the p53 gene, their expression, or their expression products.

Yet another embodiment of the invention provides genetically engineered cell lines that expresses a gene product that induces p53 mediated apoptosis, an externally controllable p53, and a gene product of a putative oncogene that inhibits the effect of the protein that induces p53 mediated apoptosis. These cell lines can be used to screen for anti-oncogene drugs according to the method of this invention.

Another, more specific embodiment of the invention is a transformed primary rodent cell line that co-expresses the E1A putative oncogene and a temperature-sensitive p53(val135) mutant. These cells undergo apoptosis at the permissive temperature (32° C.). After these cells are additionally transfected with putative oncogenes capable of suppressing apoptosis at the permissive temperature, they can be used to screen compounds with activity directed against the function of the putative oncogene, by virtue of the compound's ability to reverse the rescue from apoptosis caused by the gene product of the putative oncogene.

This invention is thus generally useful for the rapid screening of compounds and compositions that inhibit the activity of putative oncogenes. Compounds identified by this approach may have significant therapeutic value as anti-cancer drugs.

The appended claims are hereby incorporated by reference as an enumeration of the preferred embodiments.

In both 4A and 4B, transformed BRK cell lines were plated at a density of 5×10$^5$ cells per 6 cm plate at 38.5° C. 40 hours post plating the cells were trypsinized and the viable cell number per plate was determined by Trypan blue exclusion. The remaining plates were shifted to 32° C. and the viable cell number was determined following incubation for 24, 48, 72, and 96 hours. Viability is expressed as the percentage of the original viable cell number at the time of shift to 32° C. in a single experiment. (+) neo4; (Δ) neo5; (□) 3B; (o) 4B; (◊) 1A; (×) 4P.

Figure 5B:
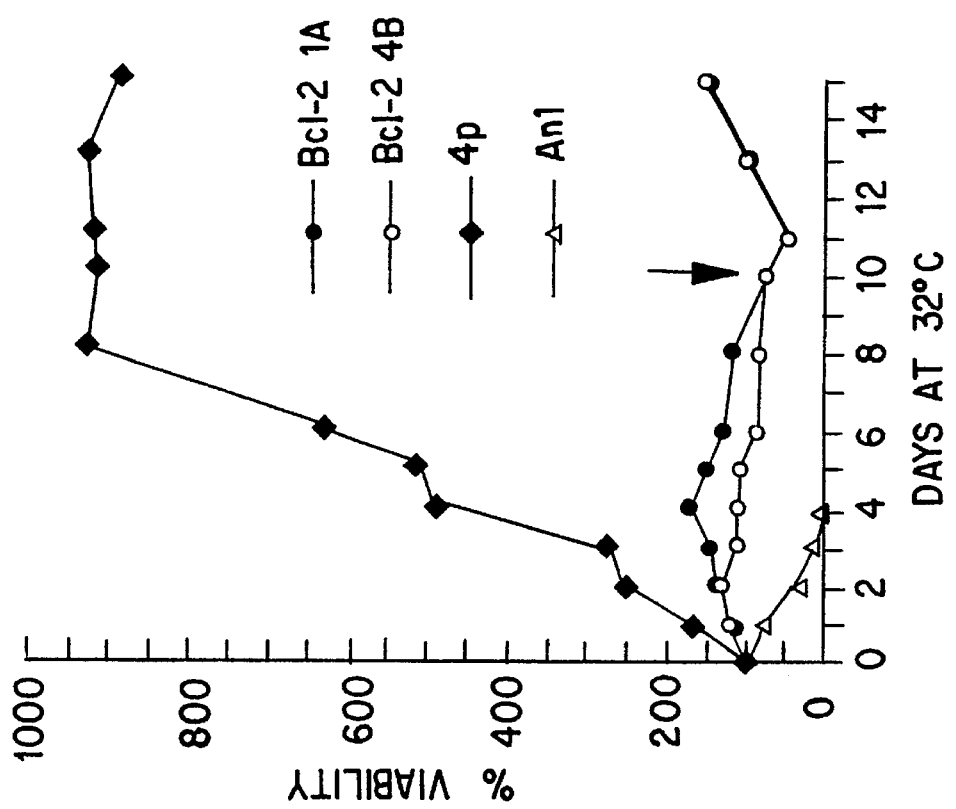
Figure 5A:
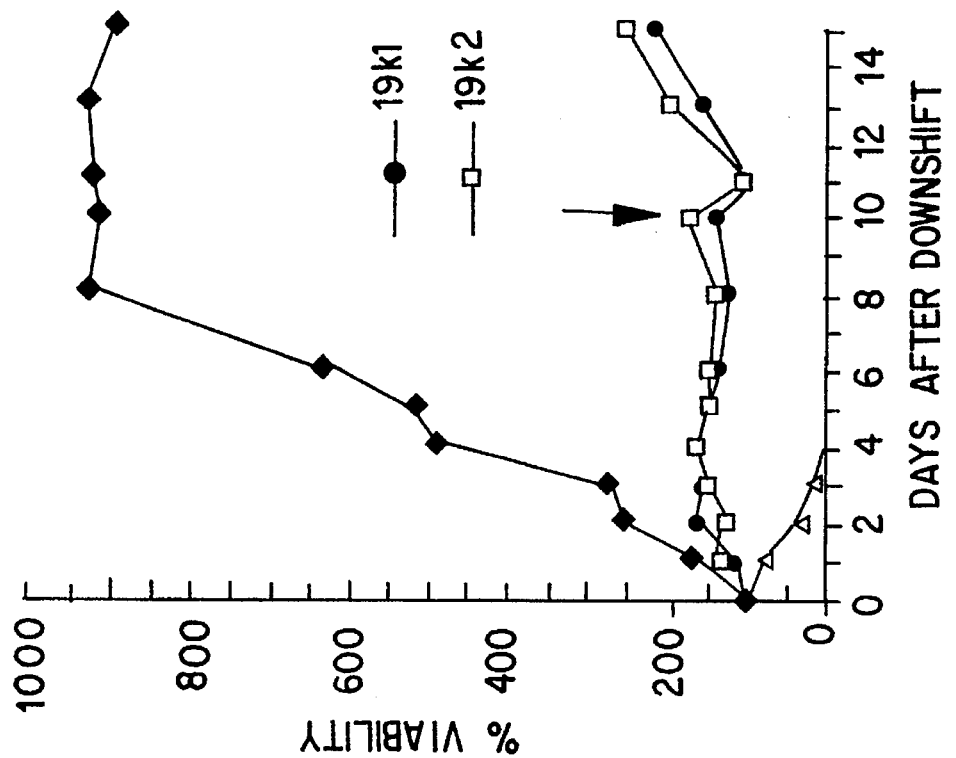

FIG. 5A shows the long term viability (absence of apoptosis) of bcl-2 or E1B(19K) cell lines grown at the nonpermissive temperature.

Figure 4A:
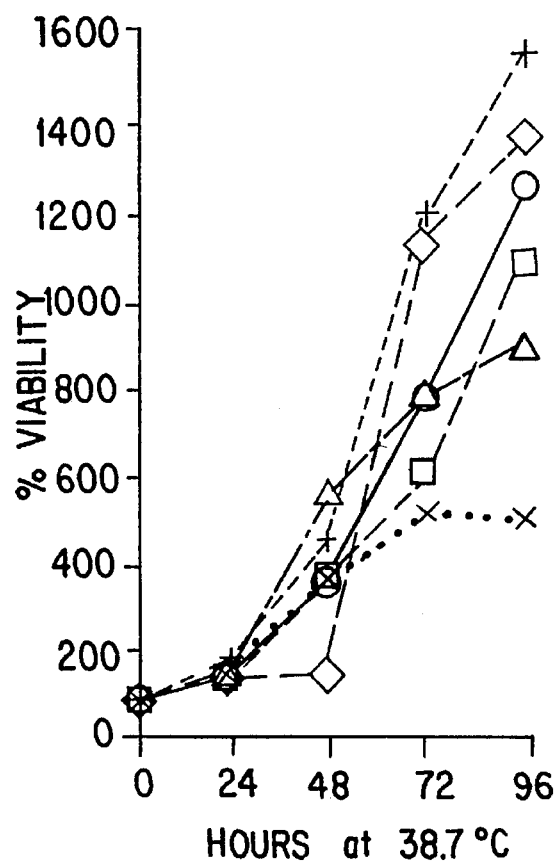
FIG. 4A shows the viability of E1A plus p53 (val 135) (neo4, neo5) and E1A plus p53(val 135) plus bcl-2 (3B, 4B, 1A) transformants at restrictive temperature.
Figure 4B:
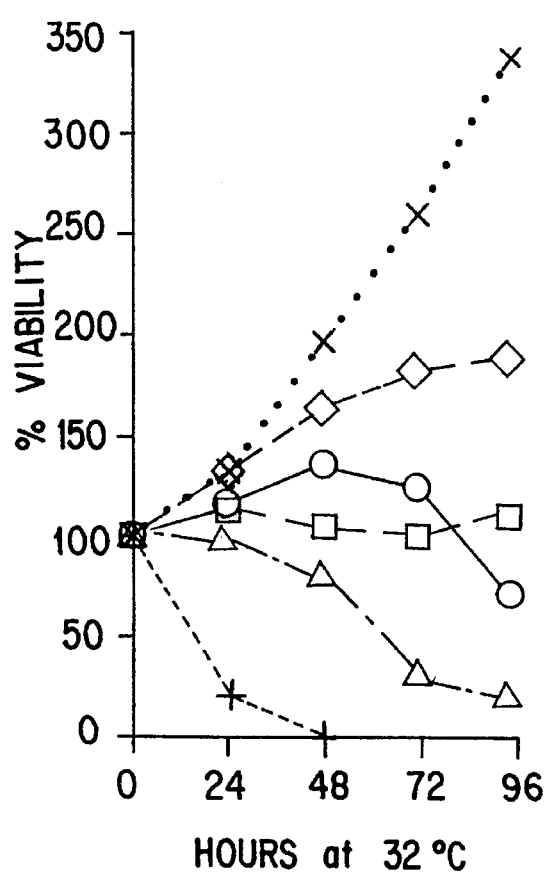
FIG. 4B shows the viability of the above-described cell lines at the permissive temperature.

FIG. 5B shows the long term viability of bcl-2 or E1B(19K) cell lines grown at the permissive temperature. Viability of Bcl-2 or E1B(19K) expressing E1A plus p53(val135) transformants, as described in FIG. 2 and FIG. 4, was determined in a single experiment over an extended period of 14 days. The arrow indicates the point at which the Bcl-2 or E1B(19K) producing lines 4B and 1A, and 19K1 and 19k2 were returned to the restrictive temperature of 38°

C. 4P, an E1A plus E1B transformant which does not contain a temperature sensitive mutation, was used as a positive control for viability at the permissive temperature. The E1A plus p53(val135) neomycin resistant transformed line p53AN1 which undergoes apoptosis at the permissive temperature served as a control for induction of apoptosis.

Figure 6:
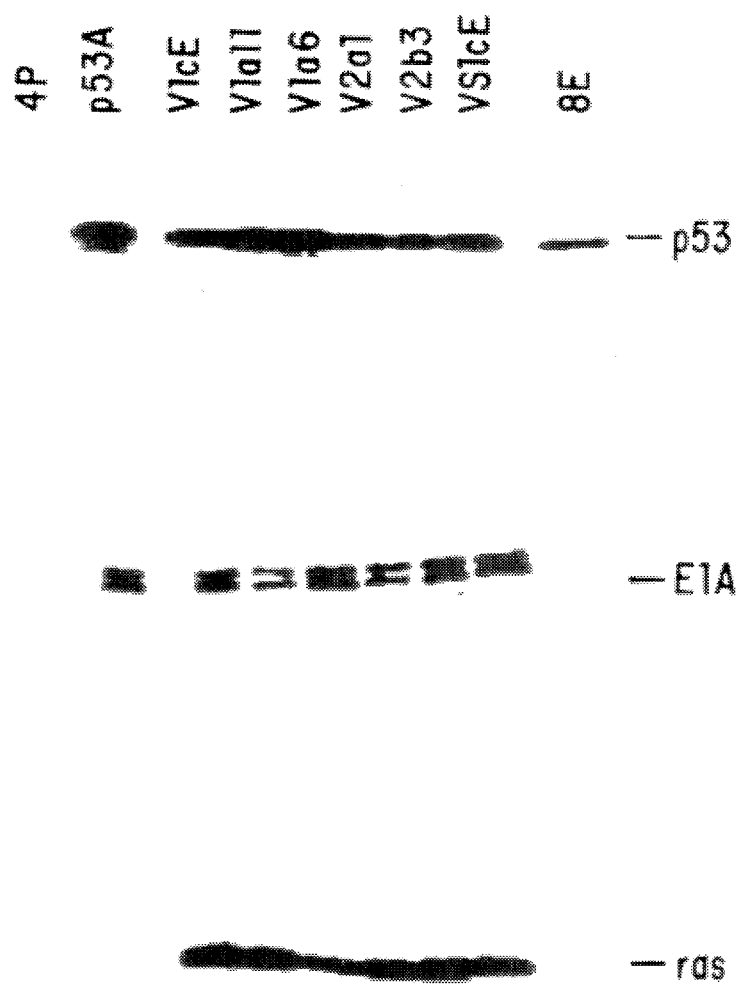

FIG. 6 shows the expression of mutant ras, p53, and E1A in ras-transformed cells. Cells containing E1A and a temperature sensitive form of p53 (val135), expressing either mutant ras (rasV) or control ras (rasVS), were grown at the restrictive temperature of 38.5° C. (where p53 is in its mutant conformation). Western blots indicate that all ras lines expressed p53, E1A, and ras.

Figure 7B:
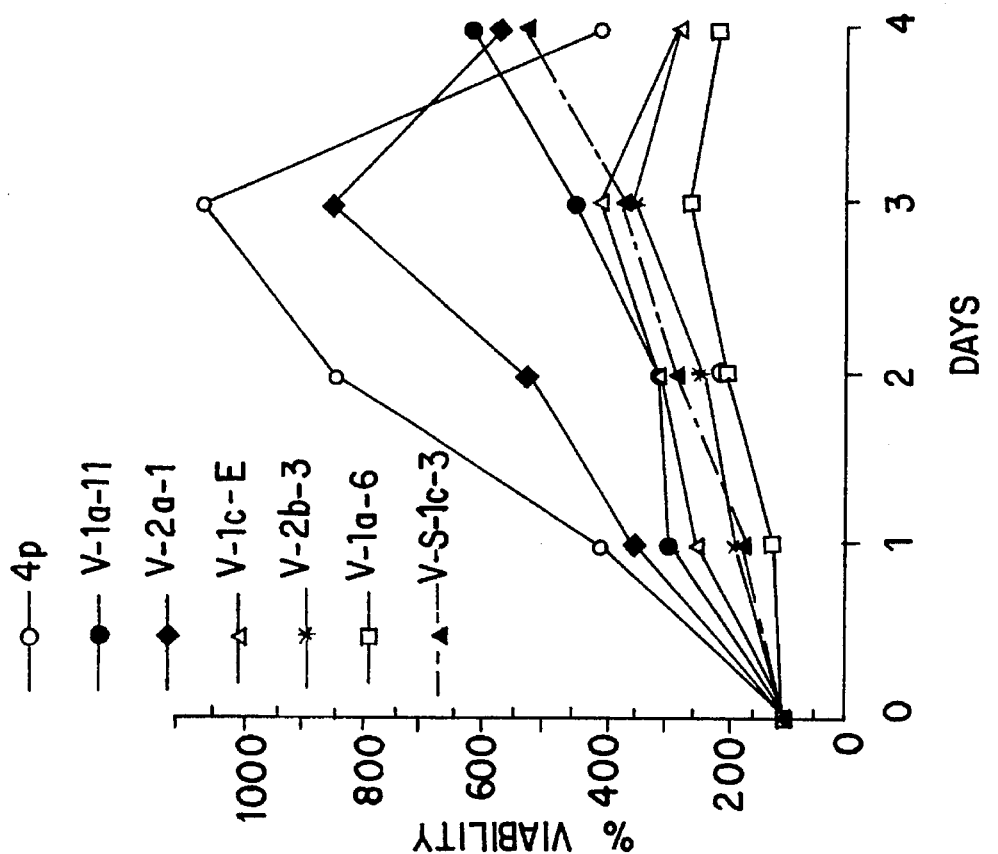
Figure 7A:
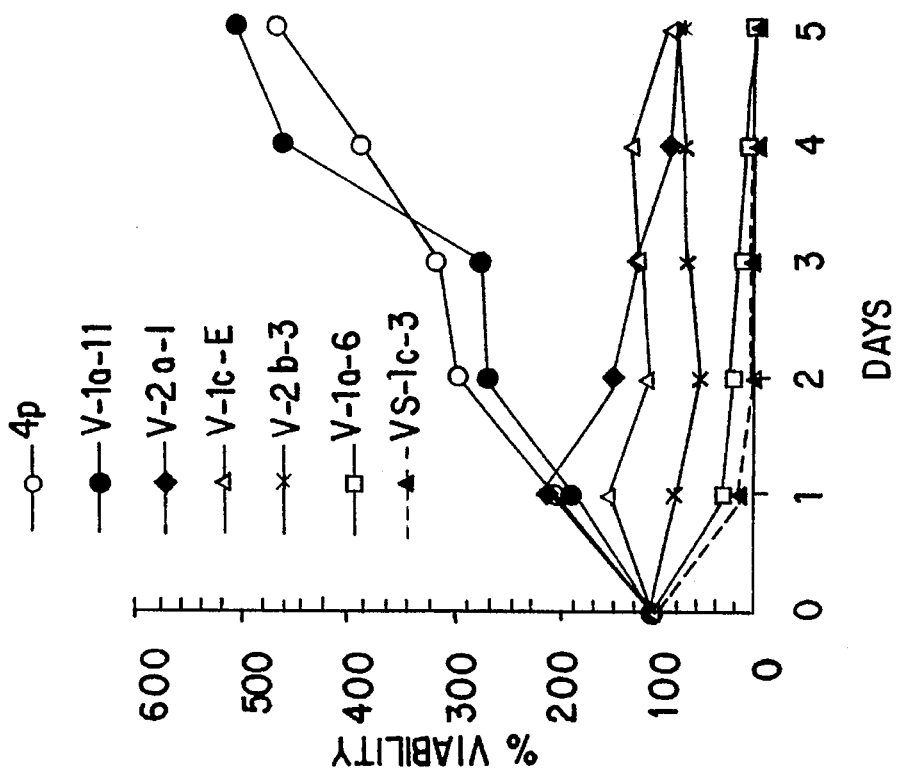

FIG. 7A shows the inhibition of p53 dependent apoptosis by activated ras at 32° C.; FIG. 7B shows the inhibition of p53 dependent apoptosis by activated ras at 38.5° C. Cell lines containing E1A and a temperature sensitive form of p53 (val135), and expressing either mutant ras (rasV) or control ras (rasVS), were shifted to 32° C., the temperature at which the temperature sensitive form of p53 reverts to its wild type conformation. Viability assays indicate that while control ras cell lines (rasVS) underwent apoptosis, rasV lines remained viable. This indicates that ras compensates for p53-associated apoptosis.

DETAILED DESCRIPTION OF THE INVENTION

The objects and advantages described above, and further objects and advantages that will be apparent to those skilled in the art, stem from several discoveries.

The most fundamental discovery upon which this invention is based is the demonstration that the apoptosis that is induced by adenovirus gene E1A is mediated by p53. Although p53 had been implicated in apoptosis in some cells, it was not known that p53 was intimately involved in E1A-induced apoptosis prior to the discovery that led to the present invention. Since non-p53 mediated apoptosis was known to occur in some cells, it was, prior to this discovery, entirely possible that E1A-induced apoptosis was caused via another mechanism.

This invention is also based on three other discoveries: that the adenovirus gene product E1B(19K), the putative oncogene bcl-2, and the putative oncogene ras each inhibit p53-mediated apoptosis. Although it was recognized that the E1B(19K) and bcl-2 genes could suppress apoptosis, the role of p53 was unknown.

These discoveries led to the making of the present invention, which is in essence was the realization that a highly simplified genetically engineered cell system could be constructed that contained the E1A gene (or another gene that could stimulate apoptosis), a p53 gene, and one of the putative oncogenes. Surprisingly, these genetic elements, when combined, produced a cell culture that was not unstable, as would be expected. Furthermore, it was found that by using a temperature sensitive mutant of p53 instead of the wild-type gene, it was possible to "turn off" the p53 gene, thus allowing the cells to grow normally. This allowed the cell cultures to be grown, multiplied, and maintained like any other cells, which facilitates long-term research and screening projects. This was highly advantageous because although the putative oncogenes were found to suppress apoptosis, they did not effectively suppress p53-mediated growth arrest, which we believe to be a phenomenon that is separate from apoptosis.

It is important to an understanding of the present invention to note that all technical and scientific terms used herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular buffers, medial reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, etc., such that a different but known way is used to achieve the same goals as those to which the use of a suggested method, material or composition is directed.

It is additionally important to recognize that although the cells used in the examples provided herein were derived from rat kidney cells, the present invention is not limited to the use of such cells. Cells from different species (human, mouse, etc.) or different tissues (breast epithelium, colon, neuronal tissue, lymphocytes, etc.) can also be used. Furthermore, even though human or viral genes have been used here, it is not intended that the invention be limited to the use of genes for any particular species or genus, but that this invention can be carried out using genes from a variety of sources. It is well within the skill of the artisan to use the described methods and cells to screen compounds that might modulate the effects of a variety of putative oncogenes from a variety of species.

Finally, it is important to note that the present invention is not limited to the use of all of the above-described discoveries or embodiments together. Although combining them may indeed be preferred, it is not necessary to the invention that all aspects be used simultaneously. For example, it is possible to use the screening method without the use of controls as a pre-screen to identify promising candidate compounds that might be further studied using this or other methods. It is also possible to use cells that contain the wild-type p53 rather than a temperature-sensitive mutant, although propagation of such cell cultures might be considerably more difficult.

It is important to a clear understanding of the present invention to understand that a number of the terms used herein are not intended to be limiting, even though common usage might suggest otherwise. For example, by the term "gene" we mean to include cDNAs, RNA, or other oligonucleotides that encoding gene products. In addition, by the term "putative oncogene" we mean not only known oncogenes, but also any gene shown to repress p53 mediated apoptosis, including, e.g., E1B(19K). Furthermore, when "expression" of a nucleic acid is mentioned, it is meant to encompass not only cellular gene expression, but also the transcription and translation of nucleic acid in cloning systems, and in any other context. By the term "p53 gene product", we mean not only the "wild type" p53 protein molecule, but also mutants and/or variants thereof, some of which are externally regulatable. We also do not intend to limit it to the p53 gene product from any particular species. In describing certain p53 gene products as being "externally regulatable", we mean that the expression of the corresponding gene, or the activity of the protein itself, may be induced or repressed at will by specifically controlling an environmental factor, such as temperature or the presence or absence of a metabolite. In referring to "wild-type" p53, we may be referring to a non-mutant p53 gene or its product, but we may also be referring to a mutant p53 that has been reverted to a functional form by the imposition of the permissive physical condition. For example, the mutant p53(Val135) protein at the permissive temperature of 32° C. might be referred to as "wild-type" p53. Whether a mutant or non-mutant p53 protein is being referred to will be otherwise apparent from the text. Lastly, although we sometimes refer to apoptosis being "inhibited" by or "blocked" by a expression of a putative oncogene, and in still other instances we refer to p53-dependent apoptosis being "compensated for" by the expression of such a gene, we do not intend to draw a distinction that has relavence to the present invention. Each has the end effect of causing apoptosis that would otherwise occur, (e.g., because of the expression of E1A), not to occur. It is the object of this invention to identify compounds that can interfere with the ability of putative oncogenes to exert this effect, irrespective of the mode of action by which the putative oncogenes do so, and irrespective of the means by which the candidate compounds might interfere with this effect.

The present invention requires that certain genes be introduced into living cellular systems. However, it is not necessary to do this in any special manner, and many appropriate methods are described in the scientific literature. Moreover, because the adenovirus E1A gene, the p53 gene, p53 mutant genes, and the bcl-2, E1B(19K),the ras gene, and the genes of many other oncogenes and putative oncogenes have been well described in the literature as well, the manner in which they can be obtained and introduced into cells are not described in detail here. However, there are some general principles that one should keep in mind in carrying out the invention, as set forth below.

The genes and gene products used in the present invention may be manipulated in a variety of both prokaryotic and eukaryotic hosts. These may include bacteria, yeast, insect cells and mammalian cells, e.g., *Escherichia coli,* COS cells, CHO cells, monkey kidney cells, and silkworm cells (sf9).

Where an exogenous gene is to be expressed in a host which recognizes its the gene's wild-type transcriptional and translational regulatory regions, the entire gene with its wild-type 5'- and 3'-regulatory regions may be introduced into an appropriate expression vector. Various expression vectors exist that employ replication systems from mammalian viruses, such as simian virus 40, adenovirus, bovine papilloma virus, vaccinia virus, insect baculovirus, etc. These replication systems have been developed to provide for markers which allow for selection of transfectants, as well as providing for convenient restriction sites into which the gene may be inserted.

Where the exogenous gene is to be expressed in a host which does not recognize the gene's naturally occurring transcriptional and translational regulatory regions, a variety of transcriptional regulatory regions may be inserted upstream or downstream from the coding region, some of which are externally inducible. Illustrative transcriptional regulatory regions or promoters for use in bacteria include the β-gal promoter, lambda left and right promoters, trp and lac promoters, trp-lac fusion promoter, and also the bacteriophage lambda $P_L$ promoter together with the bacteriophage lambda $O_L$ operator and the CI857 temperature-sensitive repressor, for example, to provide for temperature sensitive expression of the structural gene. Regulation of the promoter is achieved through interaction between the repressor and the operator. For use in yeast, illustrative transcriptional regulatory regions or promoters include glycolytic enzyme promoters, such as ADH-I and -II promoters, GPK promoter, and PGI promoter, TRP promoter, etc.; for use in mammalian cells, transcriptional control elements include SV40 early and late promoters, adenovirus major late promoters, etc. Other regulatory sequences useful in eucaryotic cells can include, for example, the cytomegalovirus enhancer sequence, which can be fused to a promoter sequence such as the SV40 promoter to form a chimeric promoter, or can be inserted elsewhere in the expression vehicle, preferably in close proximity to the promoter sequence.

When desired, expression of structural genes also can be amplified by, for example, ligating in tandem a gene for a dominant amplifiable genetic marker 5' or 3' to the structural gene and growing the host cells under selective conditions. An example of an amplifiable gene is the gene for dihydrofolate reductase, expression of which may be increased in cells rendered resistant to methotrexate, a folate antagonist.

Recombinant DNA constructs prepared for the purposes of this invention may be introduced into the host in accordance with known techniques, such as transformation, transfection using calcium phosphate-precipitated DNA, electroporation, transfection with a recombinant virus, microinjection of the DNA into cells or the like.

Once a structural gene has been introduced into an appropriate host, the host may be grown to express the structural gene. The expression vehicle may be included within a replication system for episomal maintenance in an appropriate cellular host, or may be provided without a replication system, in which case it may become integrated into the host genome. Where the promoter is inducible, permissive conditions can then be employed, for example, temperature change, exhaustion, or excess of a metabolic product or nutrient, or the like.

It is significant to note that when a mutant p53 gene is added to a cell, it is generally unnecessary to inactivate the native p53 gene(s) that may be present within the cell. The reason is that mutant p53 protein molecules are dominant over native ones in vivo. It is believed that this dominance is a result of mutant p53 polypeptides forming oligomeric structures that incorporate the native p53 subunits. Inasmuch as the mutant polypeptide is non-functional, e.g., a p53(Val135) protein at the restrictive temperature, the entire oligomeric complex will also be inactive.

The isolated genes of this invention can be used to generate modified polypeptides, each having at least one characteristic of the native polypeptide. These include subfragments, deletion mutants, processing mutants, or substitution mutants, polypeptides having the same secondary structure as the binding region of the native polypeptide, and combinations thereof. Such modified polypeptides may carry the functionality of the "wild type" peptide, or may have a modified or externally regulatable functionality. Such modified polypeptides may have considerable utility in the present invention, as would be appreciated by those skilled in the art.

Deletions in genes may be made in a number of ways known to those skilled in the art, including by enzymatically cutting the full length followed by modification and ligation of the purified fragments or by site-directed mutagenesis, for example by loop-out mutagenesis as described by Kramer et al. (1984), Nucl. Acids Res. 12: 9441–9456.

"Wild type", mutant and analogous polypeptides and compositions thereof may be used for making antibodies, which may find use in analyzing results of the assays described as part of this invention. The antibodies may be prepared in conventional ways, either by using the subject polypeptide as an immunogen and injecting the polypeptide into a mammalian host, e.g., mouse, cow, goat, sheep, rabbit, etc., particularly with an adjuvant, e.g., complete Freund's adjuvant, aluminum hydroxide gel, or the like. The host may then be bled and the blood employed for isolation of polyclonal antibodies, or the peripheral blood lymphocytes (B-cells) may be fused with an appropriate myeloma cell to produce an immortalized cell line that secretes monoclonal antibodies specific for the subject compounds.

The foregoing examples and instructions are not intended in any way to be limiting, as it should be readily apparent to those skilled in the art how alternative means might be used to achieve the results that this invention provides.

The following experimental methods, having been used by us to demonstrate and illustrate the present invention, are described in substantial detail hereinbelow. However, these details are not intended to be limiting, and those skilled in the art will appreciate that many other methods could be used to verify and explore the screening methods and cell lines that comprise the present invention.

MATERIALS AND METHODS

Plasmids and tissue culture

The p53A cell line was derived from transfection of primary baby Fisher rat kidney cells with a CMV promoter construct to express E1A (pCMVE1A)(34), and the plasmid pLTRcGval135 (22) to express murine mutant p53. The p53(val135) protein is temperature sensitive; it is predominantly in the mutant conformation at 37.5°–38.5° C. and predominantly in the wild-type conformation at 32° C. (9, 20, 22). Continuous propagation of p53A and derivatives containing the p53(val135) protein were carried out at 37.5° C. or 38.5° C. Cell lines were maintained in Dulbecco's Modified Eagle Medium with 10% fetal bovine serum.

TRANSFECTIONS

1. E1B(19K)

p53A cells were transfected with the pCMV19K plasmid and a neomycin-resistance marker by electroporation. Independent cell lines were selected with G418 and characterized for 19K expression by Western blotting with 19K-specific antibodies. Two lines, p53A19K1 and p5319K2, were evaluated further for the induction of apoptosis. Control cell lines p53An1 and p53An2, derived from p53A containing only the neomycin-resistance marker, were constructed in parallel.

2. Bcl-2

The E1A plus p53(val135) transformed BRK line p53A was transfected by electroporation with a neomycin resistance marker only (pSV2neo) or with the human Bcl-2 expression vector pSFFVbcl-2 containing a neomycin resistance marker (12). Transformants were screened for Bcl-2 expression by Western blotting (ECL) with a monoclonal antibody directed against human Bcl-2 (12). Three independent p53A clones were identified that expressed Bcl-2 (3B, 4B, 1A) in parallel with two independent control p53A derivatives that were only neomycin resistant (neo4, neo5) and were maintained at the restrictive temperature.

3. ras

The E1A plus p53(val135) transformed BRK line p53A was transfected by electropotation with the human mutant ras expression vector pneoCMVras-V containing an activated human H-ras (Val12) and neomycin resistance marker, or with pneoCMVras-VS, which is a transformation-defective control containing human H-ras(Val12) with a defective membrane targeting sequence. Transformants were screened for mutant ras expression by Western blotting (ECL) with a monoclonal antibody directed against human mutant (Val12) ras.

Five independent p53A clones were identified that expressed mutant ras: V1a-11, V-2a-1, V-1c-E, V-2b-3, V-1a-6. VS-1c-3 expressed a transformation-defective mutant, non-functional ras, and was used as a control.

WESTERN BLOTTING

Monoclonal antibodies directed against murine p53 (pAb248 and pAb2C2) were generously provided by Dr. Arnold J. Levine (Princeton University, Princeton, N.J.). The E1A specific monoclonal antibody M73 was generously provided by Dr. Ed Harlow (Massachusetts General Hospital, Chariestown, Mass.). Antibodies specific for E1B(19K) have been previously described (30), as have antibodies specific for Bcl-2 (12). Cell extracts for Western analysis were prepared from subconfluent cultures and 20 ug of protein from each cell line was analyzed by polyacrylamide gel electrophoresis and semi-dry blotting onto nitrocellulose membranes by standard procedures. Following antibody incubations, immune complexes were detected by enhanced chemiluminescence (ECL) according to the manufacturers specifications (Amersham).

The E1A plus E1B transformed BRK cell line 4P (33) was in some instances utilized as a reference for E1A expression levels.

VIABILITY AND DNA FRAGMENTATION ANALYSIS

Transformed BRK cell lines were plated at a density of $5\times10^5$ cells per 6 cm plate at 38.5° C. 40 hours after plating, when the cells were completely attached to the substrate, the cells were trypsinized and the viable cell number per plate was determined by Trypan blue exclusion. The remaining plates were shifted to 32° C. and the viable cell number was determined following incubation for increasing lengths of time. For DNA fragmentation assays, apoptotic cells were harvested from the culture medium of transformed BRK cell lines by low speed centrifugation and low molecular weight DNA was extracted by a modified Hirt procedure which permits the selective isolation of low molecular weight, degraded DNA from high molecular weight intact chromosomal DNA (11, 36). Low molecular weight Hirt supernatant fractions from BRK lines were equalized with respect to the original viable cell number at the time of the shift to 32 degrees C. Hirt DNA was analyzed by electrophoresis in a 1% agarose gel and visualized by ethidium bromide staining.

EXAMPLE 1

Figure 1:
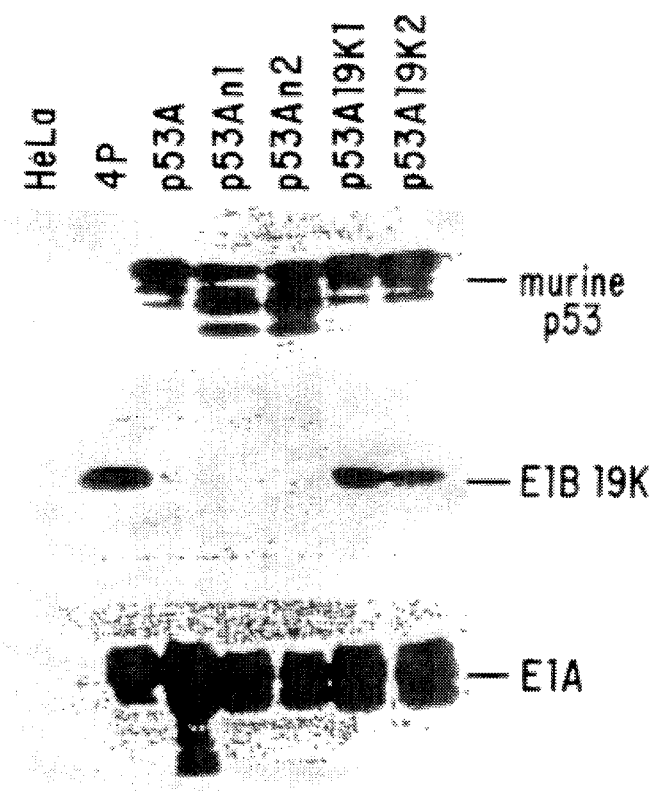
FIG. 1 shows the expression of E1A, murine p53, and the E1B 19k protein in the E1A+p53(val135) transformant p53A derivatives by Western blotting with p53, E1B 19k, and E1A monoclonal antibodies. p53A19K1 and p53A19K2 expressed the E1B 19k protein. p53An1 and p53An2 did not express the E1B 19k protein.
Figure 2A:
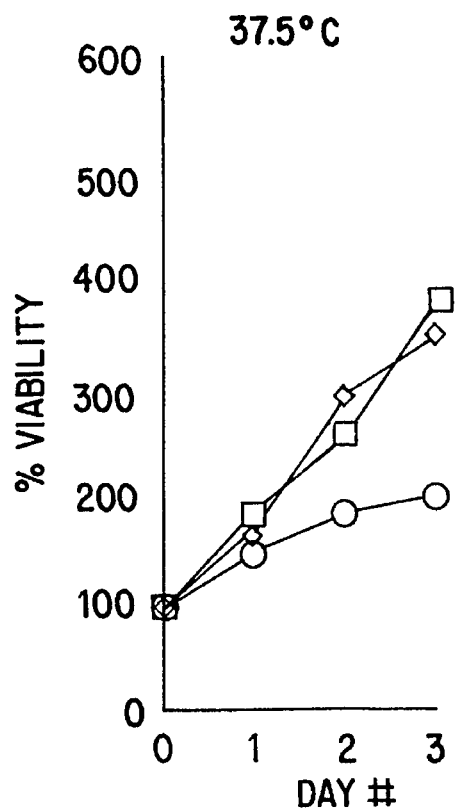
FIGS. 2A, 2B, 2C and 2D show the viability of cell lines grown at the nonpermissive temperature (37.5° C.) (FIGS. 2A and 2C) and permissive temperature (32° C.) (FIGS. 2B and 2D). Viability was determined for four independent p53A derivatives that express E1B 19K protein (FIGS. 2A and 2B) or that do not express the E1B 19K protein (FIGS. 2C and 2D). 4P in FIGS. 2A and 2B is an E1A plus E1B transformed BRK line used as a reference for E1A levels. (×) p53A19K1, (+) p53A19K2, (□) p53An1, (◊) p53An2, (o) 4P.
Figure 2B:
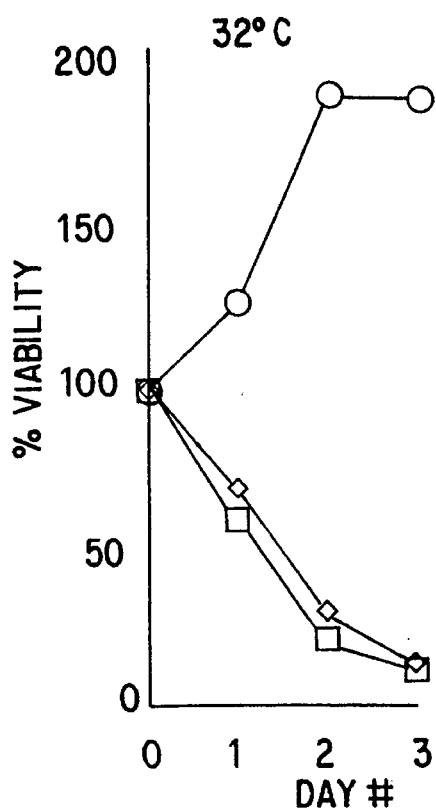
Figure 2C:
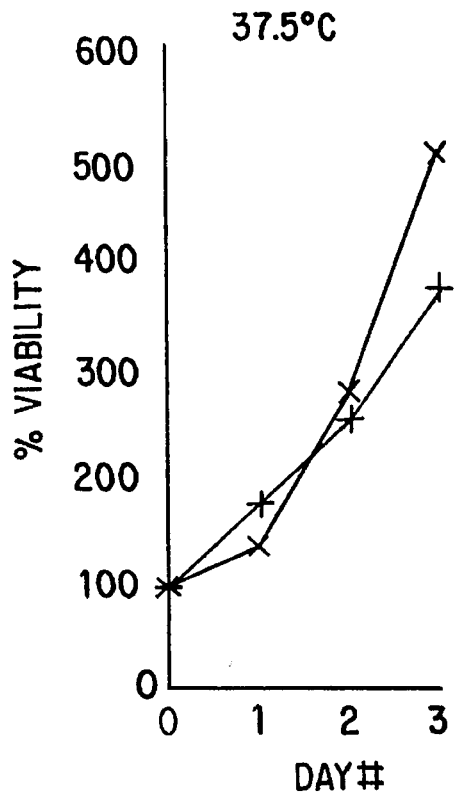
Figure 2D:
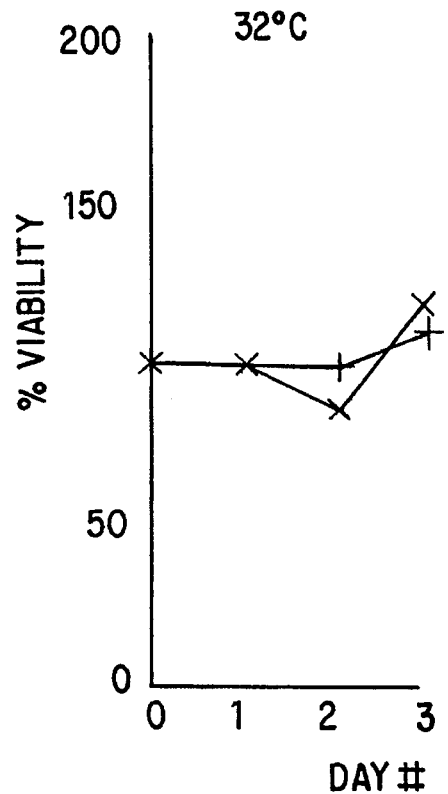

E1B(19k) Protein Blocks Induction of Apoptosis by Wild-Type p53 p53A was transfected with a neomycin-resistance marker alone or, additionally, with the E1B(19K) plasmid expression vector pCMV19K. Drug-resistant clones were screened for 19K expression by Western blotting with a monoclonal antibody for the E1B(19K) protein. Two independent p53A clones were identified that expressed the 19K protein (p53A19K1, p5319K2) in parallel with two independent control p53A derivatves that were only neomycin resistant (p53An1, p53An2)(FIG. 1). All four lines displayed similar growth rates (FIGS. 2A–2D) and morphology when maintained at the restrictive temperature (i.e., 37.5° C., the temperature at which p53(Val135) is predominantly in the mutant conformation) Therefore, E1B(19K) expression did not enhance the transformed cell phenotype or growth properties in a conspicuous way.

The ability of E1B(19K) to inhibit apoptosis upon conformational shift of p53 from the mutant to the wild type form was examined. The p53A derivatives that were merely drug resistant rapidly lost viability when shifted to 32° C. as did the original parental line p53A (FIGS. 2A–2D). The p53A derivatives that expressed the E1B(19K) protein, however, maintained viability after shift to 32° C. (FIG. 2; (×) p53A19K1, (+) p53A19K2, (□) p53An1, (◊) p53An2, (o) 4P). Expression of the E1B(19K) protein also prevented the induction of pronounced cytopathic effect that accompanied viability loss in E1A+p53(Val135) transformants. Interestingly, the 19K-expressing lines did not grow efficiently at 32° C., suggesting that 19K expression was sufficient to block apoptosis but was not sufficient to completely overcome induction of growth arrest by wild-type p53 in these lines. The growth-suppressive effect of p53 in these 19K-expressing tranformants was reversible, with cell proliferation being restored upon return to the restrictive temperature.

The integrity of chromosomal DNA was monitored as an indicator of death by apoptosis in the p53 derivatives at 37.5° C. and after shift to 32° C. Low-molecular weight (degraded) DNA was extracted from each of the four cell lines described above. Although no DNA fragmentation was apparent at the higher temperature, pronounced DNA fragmentation was induced in the 19K-minus lines after shift to 32° C., which is indicative of apoptosis (4).

EXAMPLE 2

Human Bcl-2 Expression Blocks Induction of Apoptosis by Wild-Type p53

The human bcl-2 gene was introduced into a BRK cell line previously doubly transfected with E1A and p53(val135). The triply transfected cells, maintained at the restrictive temperature, were screened for human Bcl-2 expression. Eighteen independent Bcl-2 expressing clones were isolated. Preliminary characterization of these clones indicated that they behaved similarly; characterization of three independent clones was pursued in detail.

Figure 3:
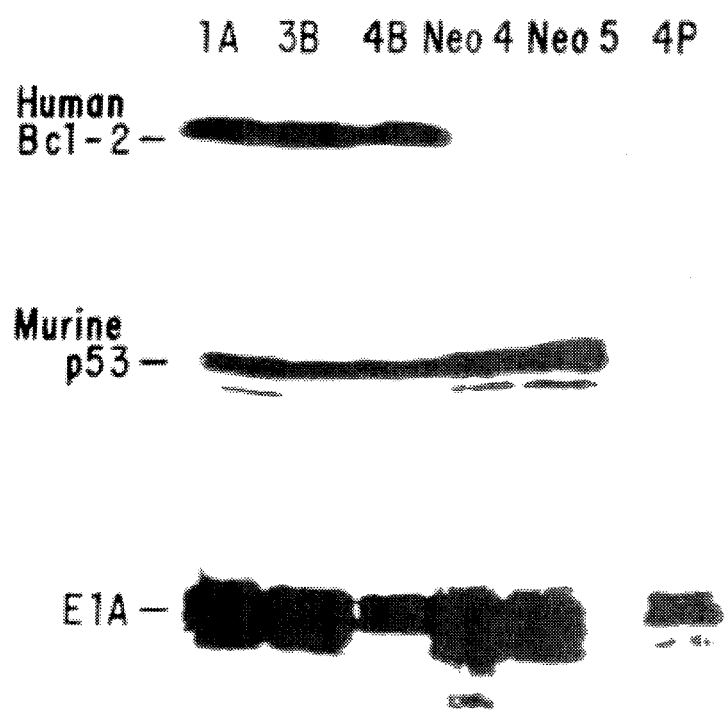
FIG. 3 shows the expression of Bcl-2 in E1A plus p53(val135) transformed rat cells. The E1A plus p53(val135) line p53A was derived from transformed foci of primary BRK cells transfected with E1A and p53(val135) expression vectors. 20 μg of cell extract for each line were analyzed for E1A, murine p53, and human Bcl-2 levels, with monoclonal antibodies M73 (E1A), pAb248 (murine p53), and 6C8 (human Bcl-2), by Western blotting. 4P is an E1A plus E1B transformed BRK line used as a reference for E1A levels. Saos2 cells do not express p53 and are a negative control for p53 levels.

The expression of Bcl-2, E1A and p53 for each of the three independent cell lines 1A, 3B and 4B are shown in the Western blots in FIG. 3. Two control lines were selected in parallel by transfection of p53A with the drug resistance marker alone. These control lines (neo4 and neo5) did not express human Bcl-2 but were drug resistant (FIG. 3). All lines expressed p53 and E1A at levels comparable to the parental p53A cell line (FIG. 3). Levels of E1A expression in the 4B line was similar to that found in the E1A plus E1B transformant 4P, whereas E1A levels were slightly higher in the other lines (FIG. 3). Murine p53 was not expressed and, therefore, not detectable in the 4P cell line (FIG. 3).

The viability of the Bcl-2 transformants and controls was monitored at the permissive and restrictive temperatures. All transformants were viable and possessed a similar rapid growth rate at 38.5° C. (FIG. 4A; (□) 3B; (o) 4B; (◊) 1A; (×) 4P). Viability was rapidly lost in the Bcl-2 negative control lines at 32° C. (FIG. 4B; (+) neo4; (Δ) neo5) and was comparable to the parental p53A line and other independently selected neomycin resistant transformants. The kinetics of viability loss among the control lines was slightly different, with one control line (neo4) losing viability more rapidly (FIGS. 4A and 4B). The growth rate appears to be inversely proportional to the death rate among E1A plus p53(val135) transformants.

After prolonged incubation at 32° C. (7 days) the survival rate among both control lines was less than 1 in $10^6$ cells (FIGS. 5A and 5B). In contrast, all three Bcl-2 expressing lines remained viable and in one case (1A) was able to sustain limited cell division at 32° C. during the course of the experiment (FIG. 4B). Subtle differences in the levels of E1A and Bcl-2 expression in the cell lines may account for these observations.

Pronounced morphological changes and DNA fragmentation are indicative of cell death by apoptosis (23) and occur upon conformational shift of p53 from the mutant to the wild-type form. At the restrictive temperature, control and Bcl-2 expressing transformants were healthy and morphologically indistinguishable from each other. After 24 hours at 32° C., the control cell lines began rounding up and detaching from the surface which was nearly complete by 72 hours. Staining the nuclei for DNA revealed the same chromatin condensation that is often associated with cells undergoing apoptosis.

The Bcl-2 expressing transformants 1A, 3B, and 4B did not undergo any gross morphological change when p53 assumed the wild-type conformation, which was seen in the control cell lines. The absence of any morphological indication of cell death in the Bcl-2 expressing cell lines at the permissive temperature indicated that the sustained viability was a result of inhibition of apoptosis and not an increased rate of proliferation relative to the rate of cell death.

DNA fragmentation in the characteristic nucleosome "ladder" pattern of cells undergoing apoptosis was coincident with viability loss and morphological changes in the control cell lines.

EXAMPLE 3

Human Ras Expression Blocks Induction of Apoptosis by Wild-Type p53

Primary BRK cells transformed by E1A and temperature sensitive p53 were transfected with mutant ras. The activated mutant ras protected cells from p53-dependent apoptosis. Conversely, cells transfected with control ras underwent apoptosis.

Cells containing E1A and a temperature sensitive form of p53 (val135), expressing either ras (rasV) or a mutant ras (rasVS), were grown at the restrictive temperature of 38.5° C. As the Western blot results in FIG. 6 show, ras, p53, and E1A were all expressed in the mutant ras-transformed cells V-1a-11, V-2a-1, V-1c-E, V-2b-3, and V-1a-6. Cells VS-1c-3 produced an inactive transformation-defective ras, and this gene product appears as ras in FIG. 6.

It is clear that activated ras compensates for p53 dependant apoptosis. Cell lines containing E1A and a temperature sensitive form of p53 (val135), and expressing either mutant ras (rasV) or control ras (rasVS), were grown at the restrictive temperature, and then were shifted to 32° C., the temperature at which the temperature sensitive form of p53 reverts to its wild type conformation. The viability assay results shown in FIGS. 7A and 7B indicate that while control ras cell lines (rasVS) underwent apoptosis, rasV lines remained viable. This indicates that ras suppresses p53-associated apoptosis.

EXAMPLE 4

A Generalized Screening Method

The preceding examples suggest that a variety of putative oncogenes may have p53-mediated functions. This further suggests that p53-mediated apoptosis may provide an ideal tool for identifying compounds and compositions that interact with putative oncogenes by testing the ability of these compounds to suppress the p53-mediated actions of the putative oncogene.

A useful first step in such screening would be to (A) add a fixed concentration of test compound to samples to genetically engineered cells that express (i) a gene product that induces p53 mediated apoptosis; (ii) a gene product for a p53 gene, wherein either the gene or the gene product are externally controllable; and (iii) a putative oncogene that inhibits the effect of the gene product that induces p53 mediated apoptosis, and (B) examine said cells to determine whether apoptosis has occurred or proliferation has been controlled or induced. For example, 10 ul of a 1 mg/ml solution of 96 compounds can be added to such cells grown and maintained at the permissive temperature in a 96-well microtiter plate. (Other concentrations may be used, based on what is known about cytotoxicity of each compound or composition.) Apoptosis will typically occur in 24–48 hours and requires minimal intervention.

If the test compounds cause cells to die or to cease proliferating, this may be due to p53-mediated events, or to general cytotoxicity. The compounds or compositions that have an effect would be further tested by serially diluting the compound to determine that minimally effective concentration. Once the minimally effective concentration is determined, the effect of the compound (administered at the minimally effective concentration to minimize side effects) would be repeated at the permissive and non-permissive temperatures, with appropriate controls, to determine if the effect is oncogene and p53 dependent. Appropriate controls would include:

1) performing the test using cells that have not been transfected with the putative oncogene; if the compounds still cause cell death, this would indicate that the mechanism of action is not putative oncogene-dependent.

2) performing the test at the nonpermissive temperature using cells that express the oncogene; if the compounds still cause cell death, this would indicate that the mechanism of action may not be p53 dependent. (Note that cell death in situation 1 and 2 would indicate general toxicity, whereas cell death in only situation 2 could indicate that the compound administered has converted mutant p53 to wild-type p53, followed by apoptosis. Detecting such compounds is also a valuable aspect of the present invention).

3) a variety of other control experiments that can readily be envisioned by those skilled in the art.

The use of apoptosis as a drug screen as described above is potentially a very powerful system for identifying compounds that modulate the biological activity of oncogenes. The technology required to set up the screen is minimal and inexpensive. Compounds identified by this approach may have significant therapeutic value as anti-cancer drugs.

REFERENCES

1. White, E., P. Sabbatini, M. Debbas, W. S. M. Wold, D. I. Kusher, and L. Gooding. 1992. The 19-kilodalton adenovirus E1B transforming protein inhibits programmed cell death and prevents cytolysis by tumor necrosis factor A, *Mol. Cell. Biol.* 12:2570–2580.

2. Bissonnette, R. P., F. Echeverri, A. Mahboubi, and D. Green. 1992. Apoptotoc cell death induced by c-myc is inhibited by bcl-2. *Nature* (London) 359:552–554.

3. Clarke, A. R., C. A. Purdie, D. J. Harrison, R. G. Morris, C. C. Bird, M. L. Hooper, and A. H. Wyllie. 1993. Thymocyte apoptosis induced by p53-dependent and independent pathways. *Nature* (London) 362:849–852.

4. Debbas, M. and E. White. 1993. Wild-type p53 mediates apoptosis by E1A which is inhibited by E1B. *Genes Dev.* 7:546 554.

5. Diller, L., J. Kassel, C. E. Nelson, M. A. Gryka, G. Litwak, M. Geghardt, and B. Bressac. 1990. p53 functions as a cell cycle control protein in osteosarcomas. *Mol. Cell. Biol.* 10:5772–5781.

6. Donehower, L. A., M. Harvey, B. L. Slagle, M. J. McArthur, J. Montgomery C. A., J. S. Butel, and A. Bradley. 1992. Mice deficient for p53 are developmentally normal but susceptible to spontaneous tumors. *Nature* (London) 356:215–221.

7. Evan, G. I., A. H. Wyllie, C. S. Gilbert, T. D. Littlewood, H. Land, M. Brooks, C. M. Waters, L. Z. Penn, and D. C. Hancock. 1992. Induction of apoptosis in fibroblasts by c-myc protein. *Cell* 69:119–128.

8. Fanidi, A., E. A. Harrington, and G. Evan. 1992. Cooperative interaction between c-myc and bcl-2 proto-oncogenes. *Nature* (London) 359:554–556.

9. Gannon, J. V. and D. P. Lane. 1991. Protein synthesis required to anchor a mutant p53 protein which is temperature-sensitive for nuclear transport. *Nature* (London) 349:802–806.

10. Henderson, S., M. Rowe, C. Gregory, D. Croom-Crater, F. Wang, R. Longnecker, E. Keiff, and A. Rickinson. 1991. Induction of bcl-2 expression by Epstein-Barr virus latent membrane protein 1 protects infected B cells from programmed cell death. *Cell* 65:1107–1115.

11. Hirt, B. 1967. Selective extraction of polyoma DNA from infected mouse cultures. *J. Mol. Biol.* 26:365–369.

12. Hockenbery, D., G. Nunez, C. Milliman, R. D. Schreiber, and S. Korsmeyer. 1990. Bcl-2 is an inner mitochondrial membrane protein that blocks programmed cell death. *Nature* (London) 348:33336.

13. Hollstein, M., D. Sidransky, B. Vogelstein, and C. Harris. 1991. p53 mutations in human cancers. *Science* 253:49–53.

14. White, E., D. Spector, and W. Welch. 1988. Differential distribution of the adenovirus E1A proteins and colocalization of E1A with the 70-kilodalton cellular heat shock protein in infected cells. *J. Virol.* 4153166.

15. Kastan, M. B., Q. Zhan, W. S. El-Deiry, F. Carrier, T. Jacks, W. V. Walsh, B. S. Plunkett, B. Vogelstein, and A. J. Fornace. 1992. A mammalian cell cycle checkpoint pathway utilizing p53 and GADD45 is defective in ataxiatelangiectasia. *Cell* 13:587–597.

16. Levine, B., Q. Huang, J. T. Isaacs, J. C. Reed, D. E. Griffin, and J. M. Hardwick. 1993. Conversion of lytic to persistent alphavirus infection by the bcl-2 cellular oncogene. *Nature* (London) 361:739–742.

17. Lowe, S. and H. E. Ruley. 1993. Stabilization of the p53 tumor suppressor is induced by adenovirus-5 E1A and accompanies apoptosis. *Genes Dev.* 7:535–545.

18. Lowe, S. W., E. M. Schmitt, S. W. Smith, B. A. Osborne, and T. Jacks. 1993. p53 is required for radiationinduced apoptosis in mouse thymocytes. *Nature* (London) 362:847–849.

19. Malkin, D., F. P. Li, L. C. Strong, J. F. J. Fraumeni, C. E. Nelson, D. H. Kim, J. Kassel, M. A. Gryka, F. Z. Bischoff, M. A. Tainsky, and S. H. Friend. 1990. Germ line p53 mutations in a familial syndrome of breast cancer, sarcomas, and other neoplasms. *Science* 250:1233–1238.

20. Martinez, J., I. Georgoff, and J. M. A. J. Levine. 1991. Cellular localization and cell cycle regulation by a temperature-sensitive p53 protein. *Genes Dev.* 5:151–159.

21. Williams, G 1991. Programmed cell death: Apoptosis and oncogenesis. *Cell* 65:1097–1098.

22. Michalovitz, D., O. Halevy, and M. Oren. 1990. Conditional inhibition of transformation and of cell proliferation by a temperature-sensitive mutant of p53. *Cell* 62:671–681

23. Wyllie, A. H. 1980. Glucocorticoid-induced thymocyte Apoptosis is associated with endogenous endonuclease activation. *Nature* (London) 356:398–400.

24. Raff, M. C. 1992. Social controls on cell survival and cell death. *Nature* (London) 356:398–400.

25. Rao, L., M. Debbas, P. Sabbatini, D. Hockenberry, S. Korsmeyer, and E. White. 1992. The adenovirus E1A proteins induce apoptosis which is inhibited by the E1B 19K and Bcl-2 proteins. *Proc. Natl. Acad. Sci. USA* 89:7742–7746.

26. Wyllie, A. J., K. A. Rose, R. C. Morris, C. M. Steel, E. Foster, and D. A. Spandidos. 1987. Rodent fibroblast tumours expressing human myc and ras genes: growth, metastisis and endogenous oncogene expression. *Brit. J. Cancer* 56:251–259.

27. Yonish-Rouach, E., D. Grunwald, S. Wilder, A. Kimchi, E. May, J. J. Lawrence, P. May, and M. Oren. 1993. p53-mediated cell death: relationship to cell cycle control. *Mol. Cell. Biol.* 13:1415–1423.

28. Yonish-Rouach, E., D. Resnitzky, J. Lotem, L. Sachs, A. Kimchi, and M. Oren. 1991. Wild-type p53 induces apoptosis of myeloid leukaemic cells that is inhibited by interleukin-6. *Nature* (London) 352:345–347.

29. Zambetti, G. P. and A. J. Levine. 1993. A comparison of the biological activities of wild-type and mutant p53. *FASEB J.* (in press).

30. White, E., S. H. Blose, and B. Stillman. 1984. Nuclear envelope localization of an adenovirus tumor antigen maintains the integrity of cellular DNA. *Mol. Cell. Biol.* 4:2865–2875.

31. Vaux, D. L., S. Cory, and T. M. Adams. 1988. Bcl-2 promotes the survival of haemopoietic cells and cooperates with c-myc to immortalize pre-b cells. *Nature* (London) 355:440–442.

32. Vogelstein, B. 1990. A deadly inheritance. *Nature* (London) 348:681–682.

33. White, E. and R. Cipriani. 1990. Role of adenovirus E1B proteins in transformation: altered organization of intermediate filaments in transformed cells that express the 19-kilodalton protein. *Mol. Cell. Biol.* 10:120–130.

34. White, E., R. Cipriani, P. Sabbatini, and A. Denton. 1991. The adenovirus E1B 19-Kilodalton protein overcomes the cytotoxicity of E1A proteins. *J. Virol.* 65:2968–2978.

35. White, E. and L. R. Goodring 1993. Regulation of apoptosis by human adenoviruses in *Apoptosis: The Molecular Basis for Cell Death II* (in press).

36. White, E., T. Grodzicker, and B. W. Stillman. 1984. Mutations in the gene encoding the adenovirus E1B 19K tumor antigen cause degradation of chromosomal DNA. *J. Virol.* 52:410–419.

37. Chiou, S., Rao, L., and E. White. 1994. Bcl-2 blocks p53-dependant Apoptosis. *Mol. Cell. Biol.* 14:2556–2563.

We claim:

1. A method for determining if a compound potentially inhibits the ability of an oncogene to modulate p53-mediated apoptosis, comprising:
   (A) adding said compound to genetically engineered cells that express:
      (i) adenovirus E1A protein;
      (ii) an externally regulatable p53 gene product; and
      (iii) an oncogene selected from the group consisting of bcl-2, ras and adenovirus E1B(19K); and
   (B) examining said cells to determine whether apoptosis has occurred, wherein the occurrence of apoptosis indicates that said compound potentially inhibits the ability of said oncogene to suppress said p53-mediated apoptosis.

2. The method of claim 1 wherein said p53 gene product is a temperature-sensitive mutant of protein p53.

3. The method of claim 1 wherein said p53 gene product is the temperature-sensitive p53 protein mutant p53(Val135).

4. A genetically engineered cell line that expresses adenovirus E1A protein, an externally regulatable p53 gene product and an oncogene selected from the group consisting of bcl-2, ras and adenovirus E1B(19K).

5. The cell line of claim 4 wherein said p53 gene product is a temperature-sensitive mutant of p53.

6. The cell line of claim 4 wherein said p53 gene product is the temperature-sensitive p53 protein p53(Val135).

7. A method for screening for a compound which acts as an anti-oncogenic drug, comprising:
   (A) adding an effective amount of said compound to genetically engineered cells that express:
      (i) adenovirus E1A protein;
      (ii) an externally regulatable p53 gene product; and
      (iii) an oncogene selected from the group consisting of bcl-2, ras and adenovirus E1B(19K);
   (B) examining said cells to determine whether apoptosis has occurred, wherein the occurrence of apoptosis indicates that said compound potentially acts as an anti-oncogenic drug by inhibiting the ability of said oncogene to suppress p53-mediated apoptosis;
   (C) performing step (A) under conditions wherein said externally regulatable p53 gene product is not expressed; and
   (D) examining said cells to determine whether cell death has occurred, wherein the absence of cell death indicates that said compound acts as an anti-oncogenic drug by inhibiting the ability of said oncogene to suppress said p53-mediated apoptosis.

8. The method of claim 7 wherein said p53 gene product is a temperature-sensitive mutant of protein p53.

9. The method of claim 7 wherein said p53 gene product is the temperature-sensitive p53 protein p53(Val135).

10. The method according to claim 1, further comprising:
   (C) performing step (A) under conditions wherein said externally regulatable p53 gene product is not expressed; and
   (D) examining said cells to determine whether cell death has occurred, wherein the occurrence of cell death indicates that said compound acts through a mechanism other than inhibition of the ability of said oncogene to modulate p53-mediated apoptosis.

* * * * *

UNITED STATES PATENT AND TRADEMARK OFFICE
CERTIFICATE OF CORRECTION

PATENT NO.   : 5,604,113
DATED        : 18 February 1997
INVENTOR(S)  : Eileen WHITE et al.

It is certified that error appears in the above-indentified patent and that said Letters Patent is hereby corrected as shown below:

| Column | Line | |
|---|---|---|
| 2 | 42 | Change "Could" to --could--. |
| 3 | 11 | Before "comprising" delete ".". |
| 6 | 8 | Change "medial" to --media,--. |
| 14 | 4 | Change "Apoptotoc" to --Apoptotic--. |
| 15 | 18 | Change "Apoptosis" to --apoptosis--. |

Signed and Sealed this

Seventeenth Day of June, 1997

Attest:

Attesting Officer

BRUCE LEHMAN

Commissioner of Patents and Trademarks